United States Patent [19]
August et al.

[11] 4,208,319
[45] Jun. 17, 1980

[54] PROCESS FOR THE PREPARATION AND USE OF SILANES

[75] Inventors: Peter August; Peter Huber; Klaus Adler; Wilfried Dressler, all of Burghausen, Fed. Rep. of Germany

[73] Assignee: Wacker-Chemie GmbH, Munich, Fed. Rep. of Germany

[21] Appl. No.: 852,129

[22] Filed: Nov. 16, 1977

[30] Foreign Application Priority Data

Dec. 9, 1976 [DE] Fed. Rep. of Germany ....... 2655877

[51] Int. Cl.$^2$ ........................... C08J 3/24; C08L 51/04
[52] U.S. Cl. ................................. 260/42.39; 556/445; 556/423; 556/429; 204/159.15; 204/159.16; 204/159.17; 260/42.29; 260/42.32; 260/42.33; 260/42.26; 260/42.37; 260/348.41; 525/100
[58] Field of Search ........ 260/827, 46.5 UA, 448.2 Q, 260/448.2 B, 375 B, 42.26, 42.29, 42.33, 42.39

[56] References Cited

U.S. PATENT DOCUMENTS

| | | | |
|---|---|---|---|
| 3,369,036 | 2/1968 | Miller | 260/46.5 UA |
| 3,427,337 | 2/1969 | Miller et al. | 260/448.2 B |
| 3,646,155 | 2/1972 | Scott | 260/827 |

*Primary Examiner*—Wilbert J. Briggs, Sr.

[57] ABSTRACT

Organosilanes containing aliphatic double bonds and a process for preparing the same which comprises reacting an organic compound having more than one aliphatic double bond with a silane having an Si-bonded hydrogen atom and at least one hydrolyzable group and/or at least one group capable of being hydrolyzed more readily than the Si-bonded hydrogen atom in the presence of a catalyst which promotes the addition of Si-bonded hydrogen atoms to aliphatic double bonds.

These organosilanes are used as reinforcing agents for compositions containing organic polymers which are crosslinked by means of sulfur or free radicals.

7 Claims, No Drawings

PROCESS FOR THE PREPARATION AND USE OF SILANES

BACKGROUND OF THE INVENTION

The present invention relates to organosilanes and a process for preparing the same. More particularly this invention relates to organosilanes containing aliphatic double bonds and their use as reinforcing additives for organopolymeric compositions.

Processes for preparing organosilanes containing aliphatic double bonds by the addition of at least one organic compound which has more than one aliphatic double bond to at least one silane having an Si-bonded hydrogen atom and at least one hydrolyzable group and/or an atom which can be hydrolyzed more readily than Si-bonded hydrogen, in the presence of a catalyst which promotes the addition of Si-bonded hydrogen to aliphatic double bonds have been described in German patent application DT-OS No. 2,244,278. Moreover, German patent application DT-OS No. 2,255,577 discloses that organosilicon compounds can be used to improve the adhesion of polymers on fillers i.e., as reinforcing additives, in compositions containing organic polymers and fillers which are crosslinked by means of sulfur or peroxides, i.e., by means of free radicals.

Compared to the reinforcing additives known heretofore, the organosilicon compounds of this invention have certain advantages. For example, when the compositions containing the organosilicon compounds of this invention are crosslinked with the aid of sulfur or free radicals, the resultant products exhibit greatly improved elongation at break, increased tensile strength and increased resistance to tear than could possibly have been obtained with the reinforcing agents known heretofore.

Therefore it is an object of this invention to provide organosilanes having aliphatic double bonds. Another object of this invention is to provide organosilanes having aliphatic double bonds which may be added as reinforcing additives to polymeric compositions which are crosslinked by means of sulfur or free radicals. Still another object of this invention is to provide polymeric compositions which exhibit improved elongation, increased tensile strength and increased resistance to tear. A further object of this invention is to provide a process for preparing organosilanes having aliphatic double bonds.

SUMMARY OF THE INVENTION

The foregoing objects and others which will become apparent from the following description are accomplished in accordance with this invention, generally speaking, by providing a process for preparing organosilanes having aliphatic double bonds which comprises reacting at least one silane having an Si-bonded hydrogen atom and at least one hydrolyzable group and/or one atom which is capable of being hydrolyzed more readily than the Si-bonded hydrogen atom with an organic compound having more than one aliphatic double bond of the general formula:

$$(H_2C=CHCH_2O)_2CRCR(OCH_2CH=CH_2)$$
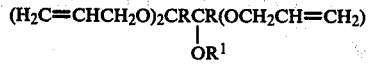

in which R represents hydrogen or the same or different monovalent hydrocarbon radicals which are free of aliphatic multiple bonds, and $R^1$ represents a monovalent hydrocarbon radical having an aliphatic double bond in the presence of a catalyst which promotes the addition of the Si-bonded hydrogen atom to the aliphatic double bonds.

The silanes prepared in accordance with the process of this invention may be represented by the formula:

$$(H_2C=CHCH_2O)_2CRCR(OCH_2CH=CH_2),$$

where R is the same as above, $R^2$ represents a bivalent hydrocarbon radical which is free of aliphatic multiple bonds, $R^3$ represents the same or different monovalent hydrocarbon radicals having from 1 to 8 carbon atoms which could be interrupted by at least 1 ether oxygen atom and n is 0, 1 or 2. These silanes can be used as reinforcing additives in compositions containing organic polymers and fillers which are crosslinked by means of sulfur or free radicals.

DETAILED DESCRIPTION OF INVENTION

All silanes having an Si-bonded hydrogen atom and at least one hydrolyzable group and/or at least one atom which is capable of being hydrolyzed more readily than the Si-bonded hydrogen atom which could have been added heretofore to organic compounds having at least one organic multiple bond can be used in the process of this invention. Silanes which may be employed in the reaction with an organic compound having more than one aliphatic double bond are those corresponding to the general formula:

where $R^3$ represents the same or different monovalent hydrocarbon radicals which are free of aliphatic multiple bonds and which have from 1 to 8 carbon atoms, X represents the same or different halogen atoms or $-OR^5$, where $R^5$ is a monovalent hydrocarbon radical which is free of aliphatic multiple bonds, which can be interrupted by an ether oxygen atom and which has from 1 to 8 carbon atoms and n is 0, 1, or 2.

Examples of radicals represented by $R^3$ are straight chain or branched alkyl radicals, such as for example the methyl, ethyl, n-propyl, isopropyl, n-butyl, sec-butyl, n-hexyl and the 2-ethylhexyl radical; cycloalkyl radicals such as for example the cyclopentyl and the cyclohexyl radicals, as well as methylcyclohexyl radicals; aryl radicals, such as for example the phenyl radical; alkaryl radicals, such as tolyl radicals and aralkyl radicals, such as the benzyl radical.

The halogen atoms X may be fluorine, chlorine, bromine or iodine atoms.

The hydrocabon radicals described above as being represented by $R^3$ are equally applicable for the hydrocarbon radicals represented by $R^5$. An additional example of a hydrocarbon radical represented by $R^5$ is the tert-butyl radical. An example of hydrocarbon radical $R^5$ which is interrupted by an ether oxygen atom is the methoxyethylene radical.

Individual examples of silanes which may be used in the process of this invention are methyldichlorosilane, dimethylchlorosilane, trichlorosilane, methyldiethoxysilane, dimethylethoxysilane, triethoxysilane and mixtures thereof.

The same catalysts which have been used or could have been used heretofore, to promote the addition of compounds having at least one aliphatic multiple bond to Si-bonded hydrogen may be used in the process of this invention. Examples of catalysts which may be used to promote the addition of Si-bonded hydrogen to aliphatic double bonds are supported and non-supported metals such as platinum, ruthenium, rhodium, palladium and iridium. These metals can be supported on carriers such as silicon dioxide, aluminum oxide or activated carbon, or they may be present as compounds or complexes of said elements. Examples of compounds or complexes of such elements are platinum halides, such as $PtCl_4$, chloroplatinic acid, $Na_2PtCl_4 \cdot 4H_2O$, platinum-olefin complexes, platinum alcohol or platinum alcoholate complexes, platinum-ether complexes, platinum-aldehyde complexes, platinum-ketone complexes and platinum-vinylsiloxane complexes, particularly platinum-divinyltetramethyldisiloxane complexes, with or without detectable halogen. Other metallic compounds which may be employed are iron, nickel and cobalt carbonyls. Compounds or complexes are often used in the form of solutions rather than as elements in order to promote the addition of Si-bonded hydrogen to aliphatic double bonds. These compounds or complexes may be dissolved in organic solvents or organopolysiloxanes, such as isopropanol, cyclohexanone, tert-butanol, or a dimethylpolysiloxane which is endblocked with vinyldimethylsiloxy groups.

When metallic platinum, platinum compounds and/or platinum complexes are used as catalysts to promote the addition of Si-bonded hydrogen to aliphatic double bonds, these catalysts are preferably used in amounts of from 0.001 to 0.02 percent by weight based on the weight of the silane used in the process.

It is preferred that the hydrocarbon radicals represented by R in the organic compounds to be added to the Si-bonded hydrogen also have from 1 to 8 carbon atoms. The examples of $R^3$ radicals described above are equally applicable to the R hydrocarbon radicals; however, it is preferred that R represent a hydrogen atom.

Although it is preferred that the radicals represented by $R^1$ have a maximum of 18 carbon atoms, they may not have less than 2 carbon atoms; otherwise they would be devoid of any aliphatic double bonds. Examples of hydrocarbon radicals represented by $R^1$ are vinyl, allyl, butenyl, hexenyl, cyclohexenyl and octadecenyl radicals. Since the allyl radical is preferred as the $R^1$ radical and since it is preferred that R be hydrogen, tetraallyloxyethane is the preferred organic compound having more than one aliphatic double bond. Mixtures containing various organic compounds having aliphatic double bonds may also be employed.

It is preferred that the organic compounds which are to be added to the Si-bonded hydrogen be used in amounts of from 1 to 2 mols per gram equivalent of Si-bonded hydrogen.

The temperature at which the process of this invention is carried out is not critical. The temperature may range from about 18° to about 180° C. Likewise, the pressure at which the process is conducted is not critical. Generally, the process is conducted at atmospheric pressure, but pressures higher or lower than 1 bar or approximately 1 bar may be used.

Although, the use of an inert solvent as a reaction medium is not required, it is not excluded.

The compounds prepared in accordance with the process of this invention are preferably represented by the general formula:

where R, $R^3$, X and n, have the same meaning as described above and $R^2$ represents a bivalent hydrocarbon radical which is free of aliphatic multiple bonds.

In the previously described processes for the preparation of organosilanes containing aliphatic double bonds, by the addition of at least one organic compound containing more than one aliphatic double bond to at least one silane having Si-bonded hydrogen, the yield of organosilane having aliphatic double bonds was no more than about 76 percent of theoretical. This is to be expected since each molecule of organic compound having more than one aliphatic double bond can react with one silane molecule having an Si-bonded hydrogen atom. However, we have surprisingly found that the process of this invention results in a yield of essentially 100 percent of theoretical of an organosilane having 3 aliphatic double bonds. At least the silane having the following formula:

which is prepared in accordance with the process of this invention need not be separated from other silanes which are obtained as a result of the addition of the organic compound having more than one aliphatic double bond to a silane having Si-bonded hydrogen, prior to its use as a reinforcing additive.

In another embodiment of this invention, the compounds having the general formula:

where R is the same as above, $R^2$ represents a bivalent hydrocarbon radical which is free of aliphatic multiple bonds, $R^3$ represents the same or different monovalent hydrocarbon radicals having from 1 to 8 carbon atoms which are free of aliphatic multiple bonds, $R^4$ represents the same or different monovalent hydrocarbon radicals having from 1 to 8 carbon atoms which may be interrupted by at least one ether oxygen atom, and n is 0, 1 or 2; are used as reinforcing additives in compositions which are based on organic polymers and fillers which are crosslinked by sulfur or free radicals.

The silanes which are used as reinforcing additives can be prepared by the direct reaction when these silanes have an Si-bonded hydrogen atom of the general formula:

However, when a silane of the following formula:

is used in the process of this invention, where X' represents a halogen atom, for example chlorine, then it is necessary to further react the reaction product with for example an organic compound having the formula:

HOR⁴, where $R^4$ is the same as above, in order to obtain a compound which can be used as a reinforcing additive in accordance with this invention. In the subsequent reaction, allyl alcohol can be used as a compound corresponding to the general formula HOR⁴. Thus in the silanes used as reinforcing additives, $R^4$ need not be free of aliphatic multiple bonds such as $R^5$. Therefore, the allyl radical may be an example of an $R^4$ radical. However, all examples of radicals represented by $R^5$ are equally applicable to the $R^4$ radicals.

It is preferred that $R^2$ represent the trimethylene radical ($-CH_2CH_2CH_2-$).

When a compound having the general formula:

$$(CH_2=CHCH_2O)_2CRCR(OCH_2CH=CH_2)$$
$$\phantom{xxxxx}|$$
$$\phantom{xxxxx}OR^2SiR_n^3(OR^4)_{3-n}$$

is added as a reinforcing additive to a composition containing an organic polymer and a filler it is preferred that it be used in an amount of from 0.1 to 10 percent by weight and more preferably from 0.5 to 2 percent by weight, based on the total weight of the organic polymer in the composition.

The organic polymeric compositions which according to this invention contain a silane as a reinforcing additive can be the same as those which have been used or could have been used in the compositions known heretofore that are based on organic polymers and fillers and which are crosslinked by sulfur or free radicals. Preferred examples of organic polymers are olefin polymers, such as natural rubber and synthetic rubber, for example styrene-butadiene-rubber, synthetic 1,4-cis-polyisoprene, ethylene-propylene-butadiene-rubber; polyethylene, polypropylene, ethylene and propylene copolymers; polyisobutylene, polybutadiene, butadiene and acrylonitrile copolymers, polystyrene, butadiene-acrylonitrile-styrene copolymers, ethylene and butene-1 copolymers and/or vinyl acetate, polychloroprene, chlorosulfonated polyethylene, chlorinated polyethylene as well as mixtures of various organic polymers.

The fillers used in the compositions containing the silanes prepared in accordance with this invention and used as a reinforcing additive can be the same reinforcing fillers and/or non-reinforcing fillers which could have been used heretofore in compositions based on organic polymers and fillers which are crosslinked by sulfur or free radicals.

In order to obtain crosslinked products having a high degree of elongation prior to break and high tensile strength as well as a high degree of resistance to tear, it is preferred that for each 100 parts by weight of organic polymer, that from 10 to 250 parts by weight of filler consisting of of a silicate, a silicon dioxide, or a colorless metal dioxide or a mixture of said substances be employed. Examples of reinforcing fillers, i.e., fillers having a surface area of at least 50 m²/gm, are pyrogenically produced silicon dioxide (fume silica), precipitated silicon dioxide having a surface area of at least 50 m²/gm, as well as silicic acid-hydrogels which have been dehydrated while maintaining their structure, pyrogenically produced aluminum oxide and pyrogenically produced titanium dioxide. Examples of non-reinforcing fillers, i.e., fillers having a surface area of less than 50 m²/gm, are quartz meal, mica, clays such as kaolin, asbestos, talcum, pigment grade titanium dioxide, aluminum oxide having a surface area of less than 50 m²/gm, diatomaceous earth, silica chalk, such as Neuberg chalk, calcium silicate, zirconium silicate and calcium carbonate, for example, in the form of ground chalk, as well as aluminum silicate. Glass can be used in the form of microglass spheres or fibers. Glass fibers and asbestos an be used in the form of mats, skeins and/or fabrics. Silicon dioxide and silicates are the preferred fillers, although fillers such as lampblack may be used.

It is preferred that the reinforcing additives prepared in accordance with this invention be crosslinked by means of sulfur in the form of elemental sulfur and/or sulfur donors, such as tetramethylthiuramdisulfide, 4,4'-dithiodimorpholine and zinc-0,0'-di-n-butylphosphordithioate. During the crosslinking, the vulcanization accelerators which are often used for vulcanization by means of sulfur as well as vulcanization retardants can of course be used. Examples of such vulcanization regulators are zinc oxide, 2-mercaptobenzothiazole, dibenzothiazyldisulfide, benzothiazylsulfenamide, dithiocarbamate, thiourea and amines.

If desired, the crosslinking of the compositions of this invention can also take place by means of free radicals. The free radicals can be obtained through high-energy rays, such as beta rays, or chemical substances. Examples of chemical substances which form free radicals are peroxide compounds and azo compounds, such as lauroylperoxide, benzoylperoxide, dicumylperoxide, tert-butylperbenzoate and azo-bis-isobutyronitrile. During the cross-linking by means of free radicals, one may of course use promoters such as cobalt, or manganese, carboxylic acid salts, tertiary amines or mercaptans.

The compositions which contain the silane reinforcing additive of this invention, organic polymer, filler, crosslinking agent and possibly a crosslinking regulator, may also contain such other materials as are generally employed in such compositions. Examples of such other substances are aging preventatives, heat stabilizers, agents which offer protection against light, ozone stabilizers, process aids, emollients, adhesives, propellants, organic acids such as stearic acid, pigments, soluble dyes, waxes and stretching aids such as sawdust.

These compositions which contain the silane reinforcing additive, organic polymer and filler and which contain at least one additional substance can be prepared by any mixing technique known in the art for preparing compositions containing an organic polymer, filler and at least one additional substance. Likewise, these compositions may be molded by any technique for molding compositions based on an organic polymer and filler. Crosslinking may take place at elevated temperatures, generally in the range of from 80° to 180° C.

As described heretofore, the compositions containing the silane reinforcing additive of this invention which crosslink with sulfur or free radicals, provide products having greatly improved elongation at break than was possible with the previously known reinforcing additives. The increase in elongation at break may be attributed to the fact that, the silane of this invention which is used as a reinforcing additive does not increase but rather decreases the crosslinking density even though it has a higher concentration of aliphatic double bonds. Still more surprisingly, it would be expected that the decrease in the crosslinking density would decrease the tensile strength of the crosslinked products; however, contrary to expectations, it was found that the decrease in crosslinking density increases the tensile strength and decreases residual compression strain.

The compositions which contain the silane reinforcing additive of this invention can be used to manufacture all objects which could have been manufactured from compositions known heretofore which were based on organic polymers and fillers and a reinforcing additive. Examples of such objects are cable covers, hoses, transmission belts, conveyor belts, roller coverings, vehicle tire surfaces, shoe soles and gaskets.

EXAMPLE 1

About 762 gm (3 mol) of tetraallyloxyethane are mixed with 2.5 ml of a solution of $H_2PtCl_6.6H_2O$ containing 1.25 percent by weight of $H_2PtCl_6.6H_2O$ in isopropanol, and heated to 90° C. in a 2-liter 3-neck flask equipped with a stirrer, an addition funnel, a reflux condenser and a thermometer. About 492 gm (3 mol) of triethoxysilane is added at such a rate through the addition funnel to the heated mixture with agitation that the temperature of the contents of the flask remains in the range of from 95° to 115° C. When all of the silane has been added, 1 ml of the $H_2PtCl_6.6H_2O$ solution is then added, and agitation of the mixture is continued at 100° C. until a sample of the mixture no longer releases any Si-bonded hydrogen when potassium hydroxide is added. Based on spectroscopic examination and elemental analysis, the reaction product corresponds to the following formula:

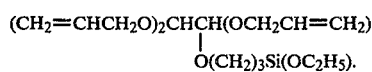

The product has the following properties:
Viscosity at 25° C. = 8.1 cSt;
$D_{25}^4 = 1.002$ gm/cm³
$M_{25}^D = 1.4414$
Iodine number = 169
The yield is about 100 percent of theoretical.

EXAMPLE 2

A mixture consisting of 100 parts by weight of commercially available ethylene-propylene-butadiene rubber having a Mooney viscosity ML 1+4—125° C. of 55 ("Keltan 512," probably a registered trademark of DSM), 100 parts of kaolin of a quality which is generally used as fillers ("Chinafill S"), 40 parts by weight of commercially available rubber plasticizer having an aniline point of 68° C. and a solidification point of −38° C. ("Kettlitz-EP-P"), 5 parts by weight of zinc oxide, 1.5 parts by weight of sulfur, 1 part by weight of stearic acid, 1.5 parts by weight of tetramethylthiuramdisulfide, 0.5 part by weight of mercaptobenzothiazole and 1 part by weight of the organosilane prepared in accordance with the procedure described in Example 1, is vulcanized, i.e., crosslinked by heating to 160° C. for 20 minutes.

Comparison Example V₁

The process described in Example 2 is repeated, except that the silane is omitted.

Comparison Example V₂

The process described in Example 2 is repeated, except that 1 part by weight of a silane having the formula:

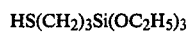

is substituted for the organosilane prepared in accordance with the procedure of Example 1.

Comparison Example V₃

The process described in Example 2 is repeated, except that 1 part by weight of a silane having the formula

is substituted for the organosilane prepared in accordance with the procedure of Example 1.

Comparison Example V₄

The process described in Example 2 is repeated, except that 1 part by weight of methacryloxypropyltriethoxysilane is substituted for the organosilane prepared in accordance with the procedure of Example 1.

Comparison Example V₅

The process described in Example 2 is repeated, except that 1 part by weight of a silane having the formula

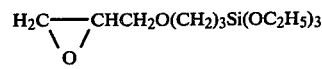

is substituted by the organosilane prepared in accordance with the procedure of Example 1.

Comparison Example V₆

The process described in Example 2 is repeated, except that 1 part by weight of bis-(3-triethoxysilylpropyl)-tetrasulfide is substituted for the organosilane prepared in accordance with the procedure of Example 1.

The following table lists the properties of the elastomers thus prepared. The crosslinking densities listed in the table were determined with a swing elastometer (manufactured by Zwick & Co. KG, 7901 Einsingen, West Germany).

TABLE

| Example or Comparison Example- | 2 | V₁ | V₂ | V₃ | V₄ | V₅ | V₆ |
|---|---|---|---|---|---|---|---|
| 100% Module N/mm² | 2.20 | 1.93 | 2.52 | 2.44 | 2.05 | 2.52 | 2.70 |
| Shore-A Hardness | 50 | 51 | 53 | 52 | 52 | 53 | 53 |
| Tensile Strength N/mm² | 6.43 | 5.38 | 6.37 | 5.49 | 5.03 | 5.66 | 6.06 |
| Elongation at Break Percent | 547 | 469 | 278 | 390 | 434 | 434 | 438 |
| Tear Resistance N/mm² | 5.0 | 3.4 | 4.9 | 4.5 | 3.8 | 4.8 | 4.5 |
| Residual Compression Srength Percent | 40.3 | 51.3 | 36.5 | 37.3 | 41.2 | 40.8 | 43.5 |
| Abrasion mm³ | 375.0 | 404.2 | 401.4 | 404.6 | 392.4 | 391.4 | 375.6 |

TABLE-continued

| Example or Comparison Example- | 2 | V$_1$ | V$_2$ | V$_3$ | V$_4$ | V$_5$ | V$_6$ |
|---|---|---|---|---|---|---|---|
| Crosslinking Density Nm | 624 | 643 | 702 | 682 | 694 | 678 | 746 |

What is claimed is:

1. A cross-linked composition which is obtained by heating at an elevated temperature a composition containing a cross-linking agent selected from the group consisting of sulfur, sulfur compounds and peroxides, an organic polymer which is capable of being cross-linked with the cross-linking agent, a filler which is present in an amount of from 10 to 250 parts by weight per 100 parts by weight of organic polymer and an organsilane of the formula $$(H_2C=CHCH_2O)_2CRCR(OCH_2CH=CH_2)$$
$$|$$
$$OR^2SiR_n^3(OR^4)_{3-n}$$

in which R is selected from the group consisting of hydrogen and monovalent hydrocarbon radicals which are free of aliphatic multiple bonds, $R^2$ is a bivalent hydrocarbon radical free of aliphatic multiple bonds, $R^3$ is a monovalent hydrocarbon radical having from 1 to 8 carbon atoms and is free of aliphatic multiple bonds, $R^4$ is selected from the group consisting of monovalent hydrocarbon radicals having from 1 to 8 carbon atoms and monovalent hydrocarbon radicals interrupted by at least one ether oxygen atom and n is 0, 1 or 2.

2. The cross-linked composition of claim 1, wherein the organosilane is present in an amount of from 0.1 to 10 percent by weight based on the weight of the organic polymer.

3. The cross-linked composition of claim 1, wherein $R^2$ is a trimethylene radical.

4. The cross-linked composition of claim 1, wherein the organic polymer is a polyolefin.

5. The cross-linked composition of claim 1, wherein the filler is a reinforcing filler.

6. A process for preparing the cross-linked composition of claim 1 which comprises heating a composition containing a cross-linking agent selected from the group consisting of sulfur, sulfur compounds and peroxides, an organic polymer which is capable of being cross-linked with the cross-linking agent, a filler which is present in an amount of from 10 to 250 parts by weight per 100 parts by weight of organic polymer and an organosilane at an elevated temperature, said organosilane having the formula $$(H_2C=CHCH_2O)_2CRCR(OCH_2CH=CH_2)$$
$$|$$
$$OR^2SiR_n^3(OR^4)_{3-n}$$

in which R is selected from the group consisting of hydrogen and monovalent hydrocarbon radicals which are free of aliphatic multiple bonds, $R^2$ is a bivalent hydrocarbon radical free of aliphatic multiple bonds, $R^3$ is a monovalent hydrocarbon radical having from 1 to 8 carbon atoms and is free of aliphatic multiple bonds, $R^4$ is selected from the group consisting of monovalent hydrocarbon radicals having from 1 to 8 carbon atoms and monovalent hydrocarbon radicals interrupted by at least one ether oxygen atom and n is 0, 1 or 2.

7. The process of claim 6, wherein the composition is heated to a temperature of from 80° to 180° C.

* * * * *